US00PP11438P

United States Patent [19]

Jamieson et al.

[11] Patent Number: Plant 11,438

[45] Date of Patent: Jul. 11, 2000

[54] STRAWBERRY VARIETY NAMED 'MIRA'

[75] Inventors: Andrew R. Jamieson, Kentville; Nancy L. Nickerson, Port Williams; Donald L. Craig, Nova Scotia, all of Canada

[73] Assignees: Atlantic Food and Horticulture Research Centre; Agriculture and Agri-Food Canada, both of Kentiville, Canada

[21] Appl. No.: 09/084,137

[22] Filed: May 26, 1998

[51] Int. Cl.[7] ..... A01H 5/00

[52] U.S. Cl. ..... Plt./208

[58] Field of Search ..... Plt./208

[56] References Cited

U.S. PATENT DOCUMENTS

P.P. 8,623 3/1994 Lopez ..... Plt./208

P.P. 10,460 6/1998 Khanizadeh et al. ..... Plt./208

OTHER PUBLICATIONS

UPOV–ROM GTITM Computer Database, 1998/04, GTI-JOUVE Retrieval Software, Citation for 'Mira'.

*Primary Examiner*—Howard J. Locker
*Assistant Examiner*—Wendy A Baker
*Attorney, Agent, or Firm*—Webb Ziesenheim Logsdon Orkin & Hanson, P.C.

[57] ABSTRACT

An ananassa type strawberry plant characterized by its high productivity and high disease resistance. The cultivar is suited for propagation in the field and produces slightly tart fruit which is acceptable for the fresh market.

1 Drawing Sheet

BACKGROUND OF THE INVENTION

The present invention includes a new and distinct cultivar of *Fragaria ananassa* known by the varietal name 'Mira', originally designated as "K84-5". The new variety resulted from a cross performed in 1982 between the unpatented cultivars 'Scott' and 'Honeoye'. The new variety first fruited at the Robinsons Corner research field of the Atlantic Food and Horticultural Research Centre, Agriculture and Agri-Food Canada in Chester Basin, Nova Scotia, Canada in 1984. The new variety was first asexually reproduced by runners in 1985 at the Atlantic Food and Horticultural Research station in Kentville, Nova Scotia, Canada. Since 1992, propagules of the new variety have been tested at the Agriculture and Agri-Food Canada research centers in Charlottetown, Prince Edward Island, Buctouche, New Brunswick and Fredericton, New Brunswick, all of Canada and at the Newfoundland Department of Agriculture field site at Pynn's Brook, Newfoundland, Canada and has been found to retain its distinctive characteristics through successive propagation.

The new variety is typical of short-day varieties and produces fruit over a four week period in northern temperate climates. 'Mira' ripens in the mid-late season, and the pattern of production is similar to the standard variety 'Kent' but three to five days later. 'Mira' has a yield substantially greater than the varieties 'Annapolis' (unpatented), 'Cavendish' (the subject of U.S. Application Ser. No. 08/535,610, filed Sep. 8, 1995), 'Blomidon' (unpatented), and 'Bounty' (unpatented) and a yield equal to 'Kent' (unpatented). The appearance of 'Mira' is superior to 'Kent' because of improvements in the uniformity of 'Mira's' fruit shape and, unlike 'Kent', the fruit color of 'Mira' does not darken excessively when over-ripe or after storage.

DESCRIPTION OF THE DRAWINGS

The accompanying photographic drawing illustrates the characteristic fruit and foliage of the new variety 'Mira', with the color being as nearly true as possible with color illustrations of this type.

DESCRIPTION OF THE PLANT

The following detailed description sets forth the characteristics of the new cultivar. Color references are made to The R.H.S. Colour Chart of The Royal Horticultural Society of London and were also determined using a Minolta Colorimeter.

Classification: The new variety is botanically classified as *Fragaria ananassa* and commercially classified as a short-day strawberry.

Plant and foliage: When propagated in the nursery, 'Mira' has similar runner production to the unpatented variety 'Honeoye' but produces more runners than 'Kent'. The leaf color of 'Mira' and 'Kent' are medium green while 'Honeoye' leaves are darker green. Comparative statistics for foliar characteristics, including leaflet measurements, serration description, and petiole pubescence are given in Table 1. Individual central (terminal) leaflets of 'Mira' are slightly longer and more narrow than those of 'Kent' and 'Honeoye'. Hence, the leaflet shape of 'Mira' is more ovate and less rounded than those of 'Kent' and 'Honeoye'. The leaflet serrations of 'Mira' and 'Kent' are semi-pointed whereas they are more rounded for 'Honeoye'. The serration at the tip of the central leaflet is small for 'Honeoye' but medium in size for 'Mira' and 'Kent'. The leaf and petiole pubescence for 'Mira', 'Kent', and 'Honeoye' are similar with the exception that 'Honeoye' has more hairs on the leaflets.

TABLE 1

Foliar characteristics for 'Mira', 'Kent', and 'Honeoye'

| | Cultivar | | |
|---|---|---|---|
| Foliar Character | 'Mira' | 'Kent' | 'Honeoye' |
| Central leaflet Length (mm) | | | |
| mean | 84.2 | 82.5 | 83.8 |
| range | 68–100 | 72–100 | 65–97 |

TABLE 1-continued

| Foliar Character | Foliar characteristics for 'Mira', 'Kent', and 'Honeoye' — Cultivar: 'Mira' | 'Kent' | 'Honeoye' |
|---|---|---|---|
| Width (mm) | | | |
| mean | 68.4 | 72.3 | 70.3 |
| range | 56–85 | 60–87 | 55–87 |
| Length/width ratio | 1.23 | 1.14 | 1.19 |
| Truss length (cm) | 28.9 | 30.6 | |
| No. leaflets/leaf | 3 | 3 | 3 |
| Leaf convexity | flat | flat | flat |
| Serrations | | | |
| Number | moderate | moderate | many |
| Shape | semi-pointed | semi-pointed | semi-round |
| Tip serration size | medium | medium | small |
| Leaf pubescence | sparse | sparse | medium |
| Petiole pubescence | | | |
| Density | sparse | sparse | sparse |
| Direction | perpendicular | perpendicular | perpendicular |
| Leaf Color | | | |
| Upper surface | Green Group 137A–137B | Green Group 137A | |
| Lower surface | Green Group 138B | Green Group 138B | |

Blooming characteristics: The length of bloom for 'Mira' and 'Kent' is about three weeks when grown in Kentville, Nova Scotia, Canada in a matted row cultural system. Flowering for both 'Mira' and 'Kent' typically begins on June 1 and ends on June 21 of each year.

Disease resistance: 'Mira' has a much higher level of resistance to red stele root rot (*Phytophthora fragariae*) than 'Kent' and 'Honeoye' and these varieties' reaction to distinct races of the pathogen are given in Table 2. 'Mira' is resistant to race A-1, A-2, and A-3 while 'Kent' and 'Honeoye' are susceptible to these races. 'Mira' and 'Kent' are moderately resistant to powdery mildew (*Sphaerotheca macularis*) but 'Honeoye' is susceptible. 'Mira' and 'Honeoye' are moderately resistant to leaf scorch (*Diplocarpon earliana*) and common leaf spot (*Mycosphaerella fragariae*) but 'Kent' is susceptible to both. 'Kent' and 'Honeoye' are resistant to green petal phytoplasma and 'Mira' is moderately resistant. 'Mira' and 'Honeoye' are less affected by fruit rot (*Botrytis cinerea*) than 'Kent'.

TABLE 2

Resistance of 'Mira', 'Kent', and 'Honeoye' to races of *Phytophthora fragariae* (red stele root rot).

| Race | Cultivar: 'Mira' | 'Kent' | 'Honeoye' |
|---|---|---|---|
| A-1 | R | S | S |
| A-2 | R | S | S |
| A-3 | R | S | S |
| A-4 | R | S or I | S |
| A-5 | S | S | S |
| A-6 | MR | S or I | S |
| A-7 | S | S | S |

S = susceptible; I = intermediate; MR = moderately resistant; R = resistant

Genetic fingerprinting of leaf extracts: Random Amplified Polymorphic DNA banding patterns with primers UBC59, UBC76, UBC85, UBC100 and UBC287 (all available from the University of British Columbia, Nucleic Acid-Protein Service Unit) distinguished 'Mira' from seven other strawberry varieties including 'Scott' and 'Honeoye', the parents of 'Mira' as shown in Table 3. The banding pattern of 'Mira' with primers UBC59, UBC85, and UBC100 was distinct from the other varieties. The primer UBC100 produced a distinct pattern for all eight varieties. This testing was done in the Biotechnology Laboratory of the Atlantic Food and Horticultural Research Centre following the techniques of Levi et al., Identification of Strawberry Genotypes and Evaluation of their Genetic Relationships Using Randomly Amplified Polymorphic DNA (RAPD) Analysis, Adv. In Strawberry Research, 13:36–39 (1994).

TABLE 3

Genetic fingerprinting of 'Mira' and seven other strawberry varieties by Random Amplified Polymorphic DNA. Bands from reliable polymorphic RAPD fragments from three replications are represented as 0 = absent or 1 = present.

| | Primer | | | | |
|---|---|---|---|---|---|
| | UBC59 | UBC76 | UBC85 | UBC100 | UBC287 |
| | Band Number for each primer and DNA pattern | | | | |
| Variety | 12345 | 123 | 123 | 12345 | 123 |
| Mira | 00111 a | 100 a | 111 a | 00111 a | 010 a |
| Scott | 10010 b | 100 a | 100 b | 00010 b | 010 a |
| Honeoye | 10011 c | 000 b | 010 c | 10100 c | 011 b |
| Totem | 10001 d | 100 a | 000 d | 11110 d | 101 c |
| Annapolis | 01111 e | 101 c | 010 c | 11101 e | 011 b |
| Cavendish | 11011 f | 101 c | 000 d | 11100 f | 111 d |
| Blomidon | 11111 g | 101 c | 010 c | 11010 g | 011 b |
| Kent | 11111 g | 100 a | 011 e | 10110 h | 011 b |

Flower and fruit production characteristics: Comparative statistics for flower and fruit characteristics near mid-season, including fruit color, are given for the three cultivars in Table 4. Flowers of 'Mira' and 'Honeoye' are positioned even with the foliar canopy but flowers of 'Kent' are above the canopy. Flowers of 'Mira' and 'Kent' are medium in size and smaller than for 'Honeoye'. Calyx size, as measured with a leaf area meter, is smaller for 'Mira' and 'Kent' than for 'Honeoye'. The calyx coloration of 'Mira' is medium green. The position of the calyx on a raised neck for 'Mira' is in contrast to the other two varieties which have a position even with the top of the berry. 'Mira' berries pick with a much longer stem than for 'Kent' and 'Honeoye'. The fruit shape of 'Mira' is conic comparted to short-conic for 'Honeoye' and ovoid for 'Kent', as confirmed by the length/width ratios. The seeds of 'Mira' are more deeply indented than those of the other two varieties. Berries of all three varieties are moderately firm but 'Mira' has tougher skin. The exterior fruit color of 'Mira' and 'Kent' is more toward orange while 'Honeoye' is more toward purple as reflected in hue angle. 'Mira' has a lighter interior than the other two varieties. The flesh coloration of 'Mira' is about RHS 41 A, becoming progressively lighter in coloration towards the core. After a 7 day period of storage, the exterior hue angle changed −6% for 'Mira', −28% for 'Kent', and −17% for 'Honeoye' indicating that 'Mira' holds its color well in storage while the other varieties darken.

TABLE 4

Flower and fruit charcateristics for 'Mira', 'Kent', and 'Honeoye'

| Character | Cultivar 'Mira' | 'Kent' | 'Honeoye' |
|---|---|---|---|
| Flower position (relative to leaf canopy) | even | above | even |
| Flower truss length | medium-long | medium-long | short-medium |
| Number of flowers per truss (average) | 11.1 | 11.2 | |
| Flower size (diameter) | medium (32.7 mm) | medium (32.4 mm) | medium-large |
| Flower color | white | white | |
| Petal spacing | touching | overlapping | touching |
| Calyx area ($cm^2$) | 3.8 | 3.9 | 6.3 |
| Calyx position | raised neck | even | even |
| Fruit stem length | very long | medium | medium |
| Fruit shape | | | |
| length/width ratio | 1.00 | 0.76 | 0.97 |
| subjective | conic | ovoid | short-conic |
| Seed position | indent | even | slight indent |
| Fruit firmness (N) | 4.6 | 4.8 | 5.2 |
| Skin toughness (g) | 15.3 | 6.2 | 9.2 |
| Color (R.H.S. Colour CHart) | | | |
| Fruit exterior | Red Group 42A | Red Group 46A | |
| Fruit interior | Red Group 41A | Red Group 44B | |
| Color (Minolta Colorimeter) | | | |
| Fruit exterior | | | |
| hue angle | 27.9 | 29.1 | 24.8 |
| chroma | 45.9 | 38.9 | 37.8 |
| lightness | 36.2 | 37.1 | 32.3 |
| Fruit interior | | | |
| hue angle | 50.2 | 47.3 | 44.2 |
| chroma | 23.8 | 28.1 | 34.6 |
| lightness | 63.0 | 55.0 | 56.1 |

Production characteristics: 'Mira' has been widely tested for several years. As shown in Table 5, 'Mira' typically yields equal to 'Kent' (the high yield standard variety in the trials). The percent of fruit classified as unmarketable is typically lower for 'Mira' than 'Kent' due to the greater resistance of 'Mira' to Botrytis fruit rot. The fruit of 'Mira' are slightly smaller (by weight) than 'Kent' and the season of harvest is consistently later than 'Kent'. Subjectively, 'Mira' has a flavor similar to 'Kent', but more tart. 'Mira' fruit will be acceptable for the fresh market and attractive to growers because of high productivity and disease resistance. 'Mira' produces abundant runners in the nursery and is readily propagated by conventional field techniques.

TABLE 5

Performance of 'Mira' and 'Kent' for 1993, 1994, 1995, and 1996 averaged over four sites: Kentville, NS; Charlottetown, PEI; Boctouche, NB; and Pynn's Brook Nfld. Plants were grown in matted rows and three blocks of 3 m long rows were harvested at each site.

| | Total Yield (t/ha) | % yield unmarketable | SIze (g/fruit) | Mean harvest (day of year) |
|---|---|---|---|---|
| 1993 | | | | |
| 'Mira' | 19.3 | 6.2 | 13.7 | 208.1 |
| 'Kent' | 21.1 | 9.0 | 14.5 | 205.7 |
| 1994 | | | | |
| 'Mira' | 24.7 | 14.2 | 12.0 | 199.9 |
| 'Kent' | 25.0 | 18.8 | 12.3 | 198.8 |
| 1995 | | | | |
| 'Mira' | 23.8 | 8.0 | 13.4 | 199.0 |
| 'Kent' | 21.5 | 10.2 | 13.9 | 197.0 |
| 1996 | | | | |
| 'Mira' | 16.1 | 11.8 | 9.8 | 198.3 |
| 'Kent' | 19.3 | 11.4 | 10.4 | 197.3 |

We claim:

1. A new and distinct variety of strawberry plant substantially as shown and described.

* * * * *

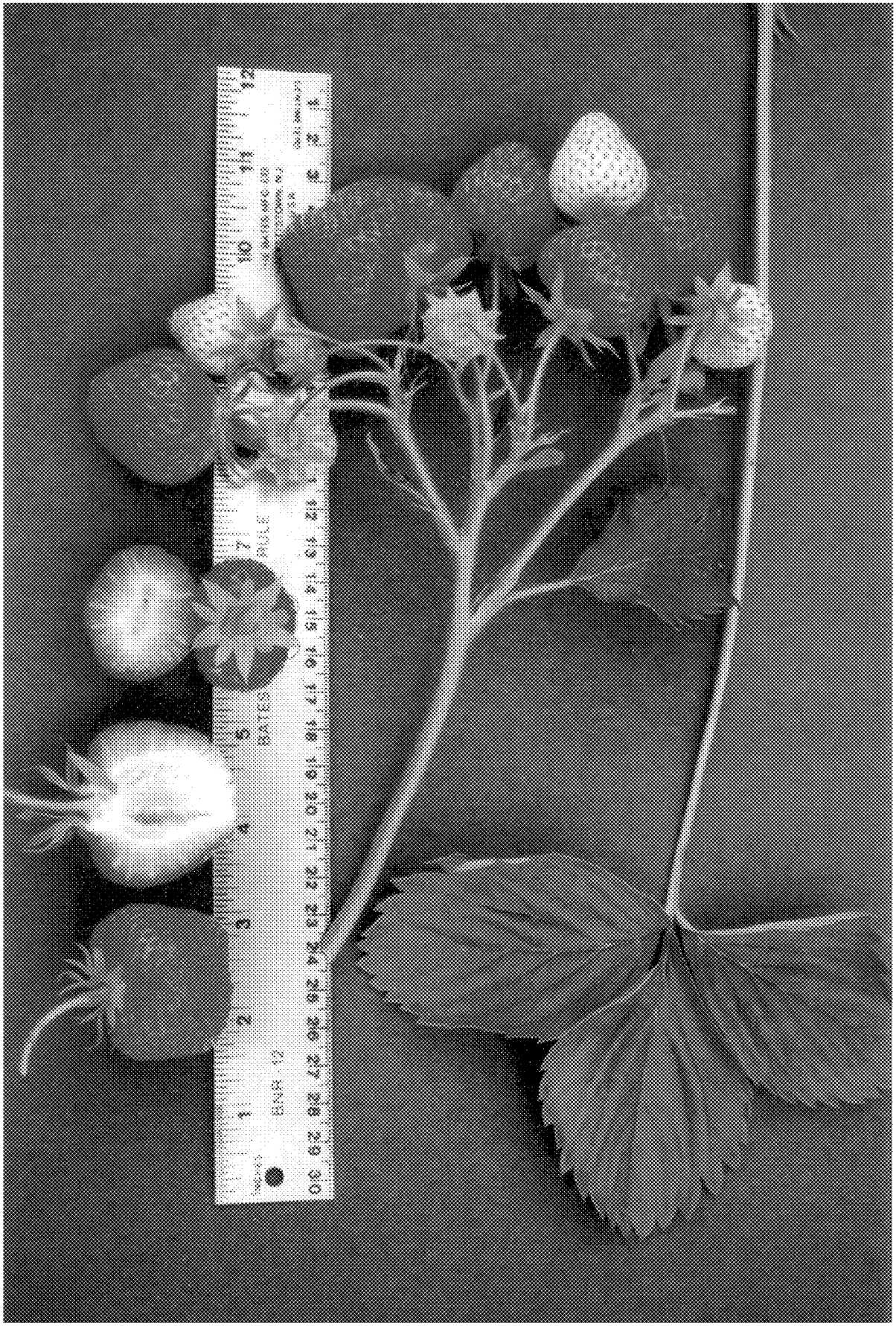
BATES
RULE
BNR 12